United States Patent [19]

DeBlase et al.

[11] Patent Number: 4,920,058

[45] Date of Patent: Apr. 24, 1990

[54] METHOD OF PREDETERMINING THE WEIGHT RATIO OF ALKENYL SUCCINIMIDE REACTANTS

[75] Inventors: Frank J. DeBlase, Hopewell Junction; Daniel T. Daly, Brewster; Rodney L. Sung; Clifton W. Wetherbee, both of Fishkill, all of N.Y.

[73] Assignee: Texaco Inc., White Plains, N.Y.

[21] Appl. No.: 322,796

[22] Filed: Mar. 13, 1989

[51] Int. Cl.$^5$ .............................................. G01N 33/44
[52] U.S. Cl. ...................................... 436/85; 436/111; 436/128; 436/129
[58] Field of Search .................. 436/85, 111, 128, 129

[56] References Cited

U.S. PATENT DOCUMENTS

| | | | |
|---|---|---|---|
| 4,401,581 | 8/1983 | Burrows et al. | 252/51.5 A |
| 4,660,151 | 4/1987 | Chipman et al. | 364/498 |
| 4,853,337 | 8/1989 | Dickakian | 436/55 |

Primary Examiner—Michael S. Marcus
Assistant Examiner—Thalia P. Vassilatos
Attorney, Agent, or Firm—Robert A. Kulason; James J. O'Loughlin; Vincent A. Mallare

[57] ABSTRACT

A method of predetermining the exact weight ratio of the reactants to produce a product and maintain the weight ratio of the reactants to obtain a maximum yield of the product. The method combines weight ratio measurement with infrared absorbance measurements to determine the maximum yield of an alkenyl succinimide product.

7 Claims, 4 Drawing Sheets

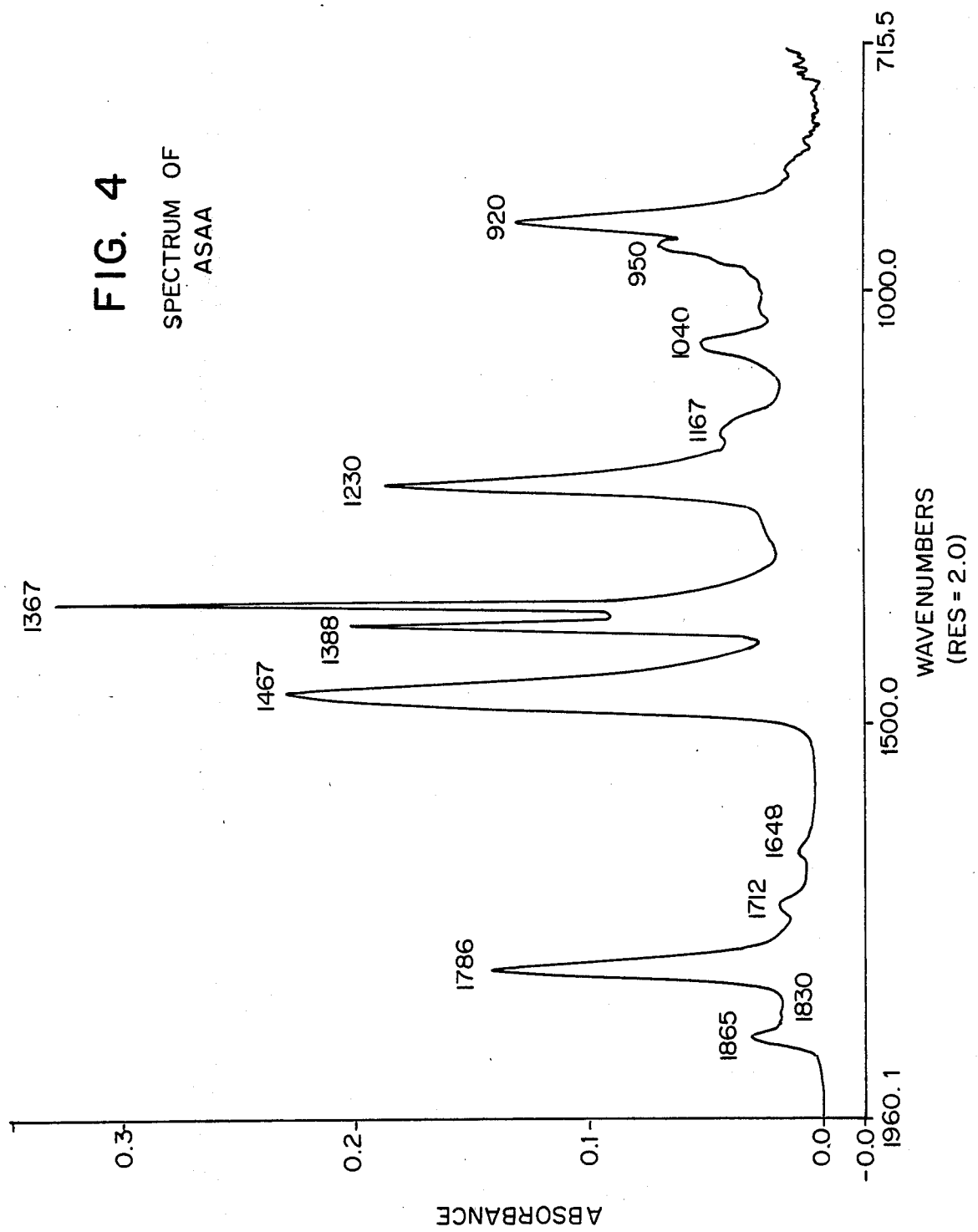

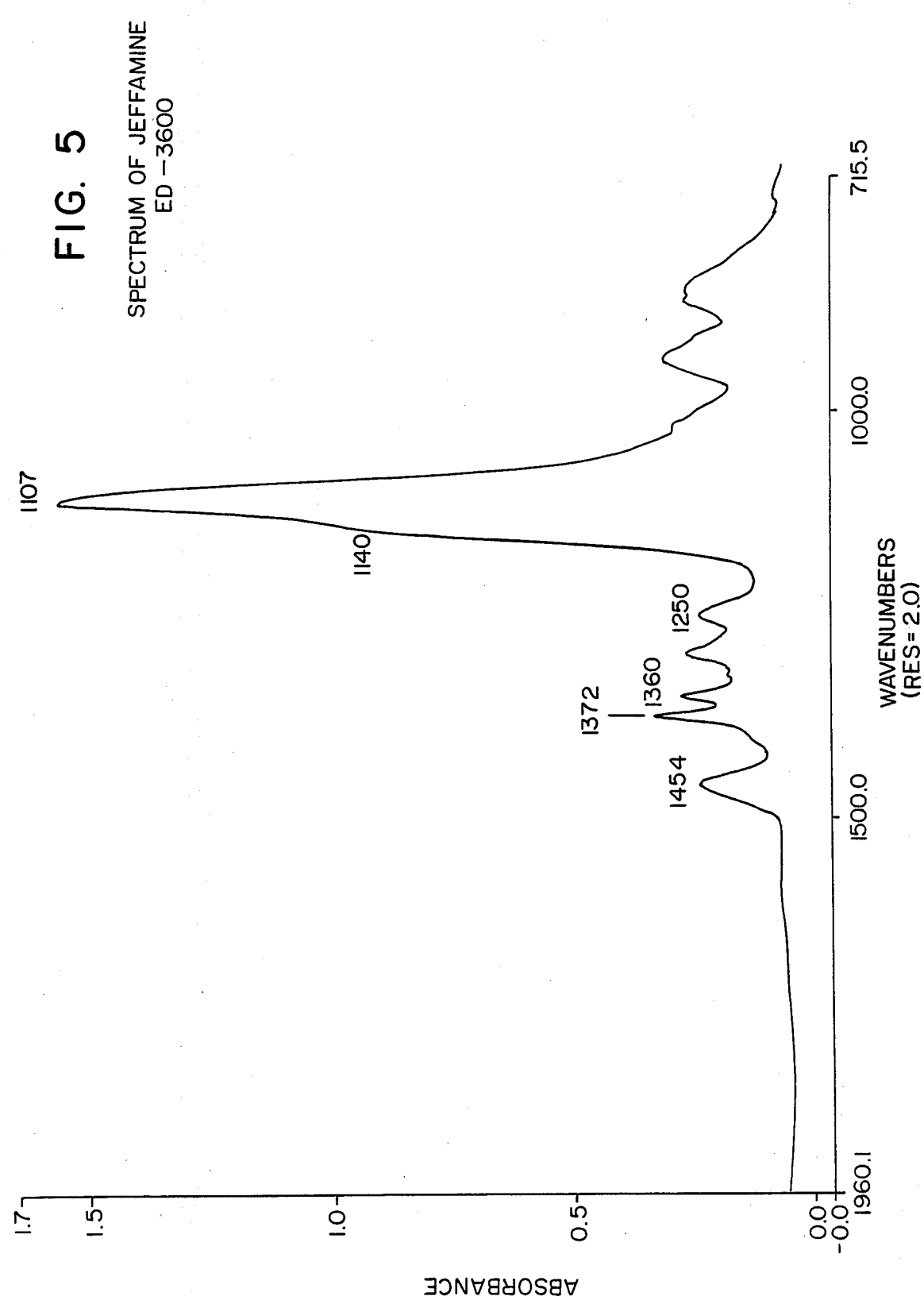
FIG. 5 SPECTRUM OF JEFFAMINE ED-3600

METHOD OF PREDETERMINING THE WEIGHT RATIO OF ALKENYL SUCCINIMIDE REACTANTS

BACKGROUND OF THE INVENTION

This invention relates to a method for producing an ORI additive for motor fuels such as gasolines. More particularly, it relates to a method of predetermining the weight ratio of the reactant needed to produce such desired ORI additive product.

In this application, the inventors are primarily concerned with determining weight ratio of the reactants necessary to produce a maximum amount of an ORI additive.

Up to the present time, the exact amounts of each reactant or the weight ratios of reactants were determined by a saponification method. This saponification method generally provided only an approximate amount or weight ratio of the reactants needed to produce the ORI additive. By using this saponification method there is a waste of time and materials to provide the correct amounts or weight ratio of the reactants needed to produce the desired ORI additive.

Thus, it is an object of the present invention to provide a means of determining exactly the amount or weight ratio of the reactants to provide a maximum amount of the desired ORI additive for a motor fuel composition.

DISCLOSURE STATEMENT

U.S. Pat. No. 4,053,743 discloses a method for controlling the pH and other concentration variables of a controlled feed component, wherein when at least one desired outlet concentration or a function dependent on outlet concentration is given, initially the apparent output concentration of at least one other feed component is calculated with the aid of the inlet concentration and the residence time distribution of the controlled feed component from the inlet to the outlet flow thereof.

U.S. Pat. No. 4,060,716 discloses a method and apparatus for automatically monitoring dynamic signals, such as from vibration sensors in an operating industrial or other plant, to identify abnormal events and as an abnormal vibration from a reactor, due to failure, draw conclusions as to their severity and indicate the action to be taken. In such method a computer is used to control the scanning of one or two sensor channels at a time through a matrix of analog switches.

U.S. Pat. No. 4,321,680 discloses a spectrum analyzer for Fast Fourier Transform (FFT) analyzing and displaying the frequency of a digital signal over a given frequency band (background), as well as over a more limited frequency band (foreground). The spectrum of the signal over each frequency band is calculated and displayed so as to appear on a screen as a simultaneous display. The position of the limited frequency band, as well as the width thereof, may be varied.

U.S. Pat. No. 4,511,986 discloses a method and apparatus for simultaneously recording multiple Fourier Transform Infrared (FT-IR) signals using an interferometer. The analog signals are coupled to switching means which is operable in response to a first control signal for synchronizing the operation of the interferometer and the control circuits and a second control signal for defining data acquisition intervals to direct the sampled data of the analog impact signals over a circuit path including Sample and Hold and Analog to Digital Conversion circuits to a processor for storing the digital data corresponding to the analog input signals. The switching means is operated so that samples of the analog input signals are taken in sequence and stored in sequential storage locations in interleaved fashion. The processor is operable under program control to access the digital data so that all data samples for the same input signals are separated to produce an interferogram for each of the input signals. These interferograms can then be Fourier Transformed to produce spectra in the usual manner.

U.S. Pat. No. 4,725,140 discloses a coherent light beam which is made incident upon a cell via a polarizer. In the cell is combined a reaction liquid consisting of the fine magnetic particles which have an antibody coated thereon and a sample containing an antigen which is specifically reacted with the antibody on the particles. The particles are rotated in the reaction liquid by means of alternating magnetic fields having a frequency $f_o$ and generated by coils arranged beside the cell. Light scattered by the particles is made incident upon a photodetector via a polarizer whose polarization plane is perpendicular to that of the analyzer. An output signal from the photodetector is synchronously detected by means of a reference signal having a frequency $2f_o$. Then a synchronously detected output signal represents an amount of the antigen contained in the sample.

U.S. Pat. No. 4,762,413 discloses a coherent laser light flux projected into a cell made of transparent quartz and light scattered from particles suspended in an antigen-antibody reaction liquid contained in the cell, detected by a photomultiplier by means of a colimator. An output electrical signal from the photomultiplier is sampled at different time instances and samplings are supplied to a fast Fourier transformer to derive a plurality of power spectrum densities of fluctuation in intensity of the scattered light. A plurality of power spectrum densities are averaged to generate a mean power spectrum density. An amount of antigen contained in the reaction liquid is measured in accordance with the mean power spectrum density.

U.S. Pat. No. 4,660,151 discloses a multicomponent quantitative analytical method and apparatus using IR spectrometry to determine amounts and species in a process.

SUMMARY OF THE INVENTION

This invention provides a method of predetermining the exact weight ratio of the reactants necessary to provide a maximum amount of a desired product. The method comprises:

(a) determining by spectrometry the characteristic IR absorption of the functional group of each reactant and that of the product desired;

(b) establishing the weight ratio to the IR absorption ratio of the reactants to produce the desired product whereby a first curve is formed of the reactant IR absorption ratio versus the reactant weight ratio;

(c) varying the weight ratio of the reactants in simulated small scale reactions of the method to produce the product and using the product characteristic IR absorption to form a second curve of the product IR absorption versus the reactant weight ratio, thereby determining the reactant weight ratio necessary to produce the maximum amount of said product;

(d) using the reactant weight ratio determined from the second curve, determine from the first curve the optimum IR absorption ratio of the functional groups of the reactants; and (e) comparing the prior measured IR absorption ratio of the reactant mixture being charged with the determined optimum reactant IR absorption ratio, whereby the exact weight ratio of the reactants is measured prior to heating and, if necessary, corrected to produce the maximum amount of the product.

According to the present method for predetermining the exact weight ratio of the reactants necessary to produce the ORI control additive of an alkenyl succinimide, the reactants may be polyethoxy polypropoxy polybutoxy diamine and an alkenyl succinic anhydride.

BRIEF DESCRIPTION OF THE DRAWINGS

The advantages of the present invention are more apparent when considering the following drawings with the detailed discussion of the present invention. The drawings are:

FIG.4 is a graph showing the absorbance versus the wavenumbers of each of the reactants of the present invention; and FIG.5 is a graph showing the relationship of the IR absorption versus the wavenumbers of the functional group of each reactant.

DETAILED DESCRIPTION OF THE INVENTION

Figure 1:
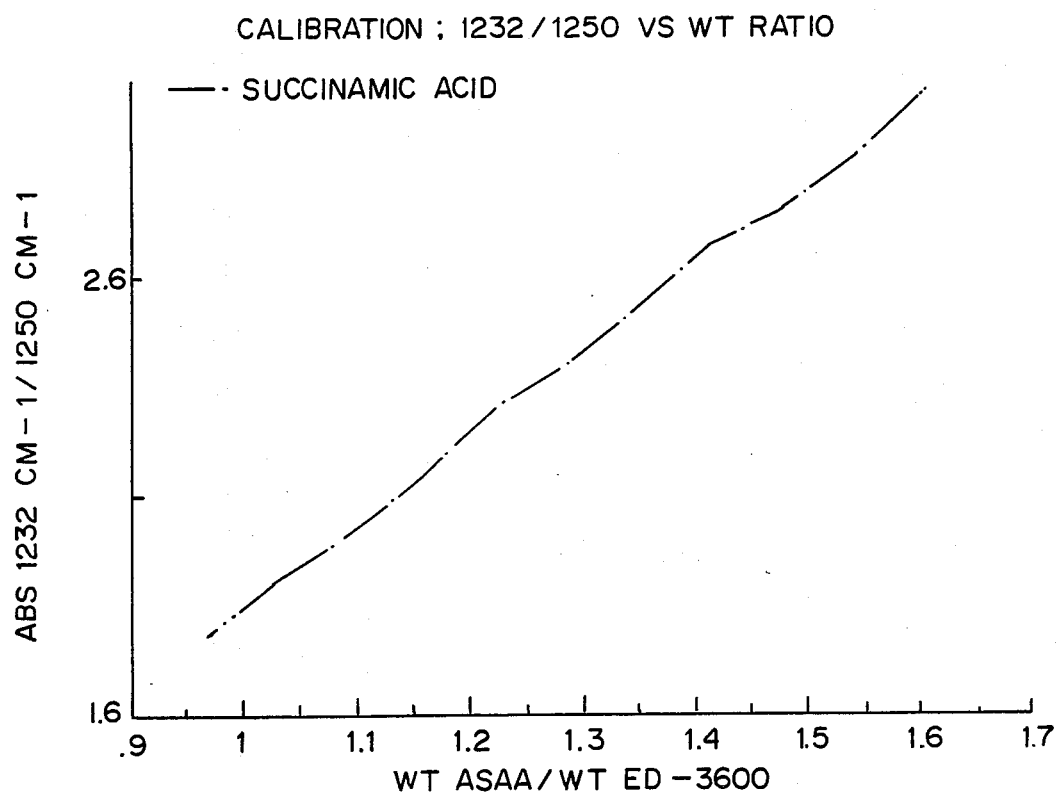
FIG.1 is a graph, i.e., first curve, showing the relationship of the characteristic reactant IR absorption ratio versus the reactant weight ratio as to succinamic acid.

The present method of predetermining the exact weight ratio of the reactants necessary to produce a desired product has been developed to facilitate the production of an ORI control additive.

According to the present invention, the exact weight ratio of the reactants necessary to produce the maximum amount of desired product, an ORI control additive, is predetermined before the actual full-blown reaction is carried out to produce such desired product, a ORI control additive.

According to the present invention, it is intended that the concept and teaching thereof may be used as effectively in producing any product in any industry or discipline including the pharmaceutical and chemical industries.

The general method that may be used for predetermining the exact weight ratio of the reactants necessary to produce a desired product comprises the steps of:

(a) determining by spectrometry the characteristic IR absorption of the functional groups of each reactant and that of the product desired;

(b) establishing the weight ratio to the IR absorption ratio of the reactants to produce the desired product whereby a first curve is formed of the reactant IR absorption ratio versus the reactant weight ratio;

(c) varying the weight ratio of the reactants in simulated small scale reactions of the method to produce the product and using the product characteristic IR absorption to form a second curve of the product IR absorption versus the reactant weight ratio, thereby determining the reactant weight ratio necessary to produce the maximum amount of the product;

(d) using the reactant weight ratio determined from the second curve, determine from the first curve the optimum IR absorption ratio of the functional groups of said reactants; and (e) comparing the prior measured IR absorption ratio of the reactant mixture being charged with the determined optimum reactant IR absorption ratio, whereby the exact weight ratio of the reactants is measured prior to heating and, if necessary, corrected to produce the maximum amount of the product.

The desired product, i.e., the ORI control additive, of the present invention is a ($C_{33}$–$C_{330}$) alkenyl succinimide produced from a reaction of reactants of (1) a polyethoxy polypropoxy polybutoxy diamine and (2) a ($C_{33}$–$C_{330}$) alkenyl succinic anhydride.

The functional groups of the respective reactants (1) diamine and (2) anhydride are, respectively, ethylene oxide and polyisobutenyl (PIB).

Prior to reacting the reactants to produce the ORI control additive, the IR absorption ratio of the reactant mixture being charged is measured from about 2000 $cm^{-1}$ to about 700 $cm^{-1}$.

In measuring and predetermining the exact weight ratio of the reactants to produce the product, an ORI control additive—a ($C_{33}$–$C_{330}$) alkenyl succinimide, the prior measured IR absorption ratio of the reactant mixture being charged is compared with the determined optimum reactant IR absorption ratio so that the exact reactant weight ratio is measured prior to heating the reactant mixture and, if necessary, the reactant weight ratio is corrected to produce the maximum amount of the product, an ORI control additive—a ($C_{33}$–$C_{330}$) alkenyl succinimide. The alkenyl group referred to herein may have from about 33 to about 330 carbon atoms.

The present method of predetermining the exact weight ratio of the reactants necessary to produce the maximum amount of the desired product involves the extensive use of spectrometry and graphs and curves which are illustrated in the drawings as described herein.

The graphs and curves are the result of determinations made by spectrometry. The graphs and curves illustrate the important properties of the elements such as the IR absorption of the functional groups of the respective reactants as well as that of the desired product.

Initially, in determining the exact weight ratio of the reactants, the characteristic IR absorption of the functional group of each reactant as well as that of the desired product is determined by spectrometry. Specifically, the characteristic IR absorptions are determined from FIG.5 for the functional group of the polyethoxy polypropoxy polybutoxy diamine, the ether linkage, i.e., ethylene oxide. That of the functional group of the succinic anhydride which is polyisobutenyl (PIB) determined from FIG.4 and that of the desired product is determined from FIG.3.

In predetermining the exact weight ratio of the reactants to produce the desired product, a procedure was carried out in successive steps as outlined and discussed in the following procedure. In the procedure there is reference to the drawings, i.e., figures (FIGS.1-5).

THE EXACT PROCEDURE FOR DETERMINING REACTANT WEIGHT RATIO

The following is a specific procedure for a reaction which was carried out on a large scale in which the exact molecular weights of the reactants could not, up to that time, be determined accurately or accurately have a molecular weight distribution, i.e., of polymers.

The first step is to take an infrared spectrum of each reactant. Then, an analysis of each spectra is made to identify unique absorbances due to structural features of the reactants.

For the reaction of Jeffamine ED-3600 (polyethoxy polypropoxy polybutoxy diamine) and ASAA (alkenyl succinimic anhydride), the IR spectra were recorded. In FIG.4 the spectrum for ASAA, the absorbances from 1960 $cm^{-1}$ to 715.5 $cm^{-1}$ were assigned structural features. In FIG.5 the spectrum for the diamine (Jeffamine ED-3600) the absorbances were assigned in the same manner as above. Thus, a complete analysis of both IR absorbances of the reactants was obtained. After each unique absorbances had been identified, an absorbance corresponding to a structural feature in each reactant, which will not change during the course of the reaction, was chosen.

From FIGS. 4 and 5, the IR absorbances of 1232 $cm^{-1}$ and 1250 $cm^{-1}$ were chosen respectively. The main reason, as explained in this first step was that, these represent structural features of the reactant which would not change during the reaction.

The second step of the procedure was the recording of the IR spectra of a broad range of weight ratios of reactants so that a plot could be constructed of the IR ratio of the chosen peaks (see FIG.4) vs the weight ratio of the reactants. This could be done at any time during the course of the reaction, i.e., the weight ratio could be obtained by the measurement of the IR spectrum (see FIG.1).

Figure 2:
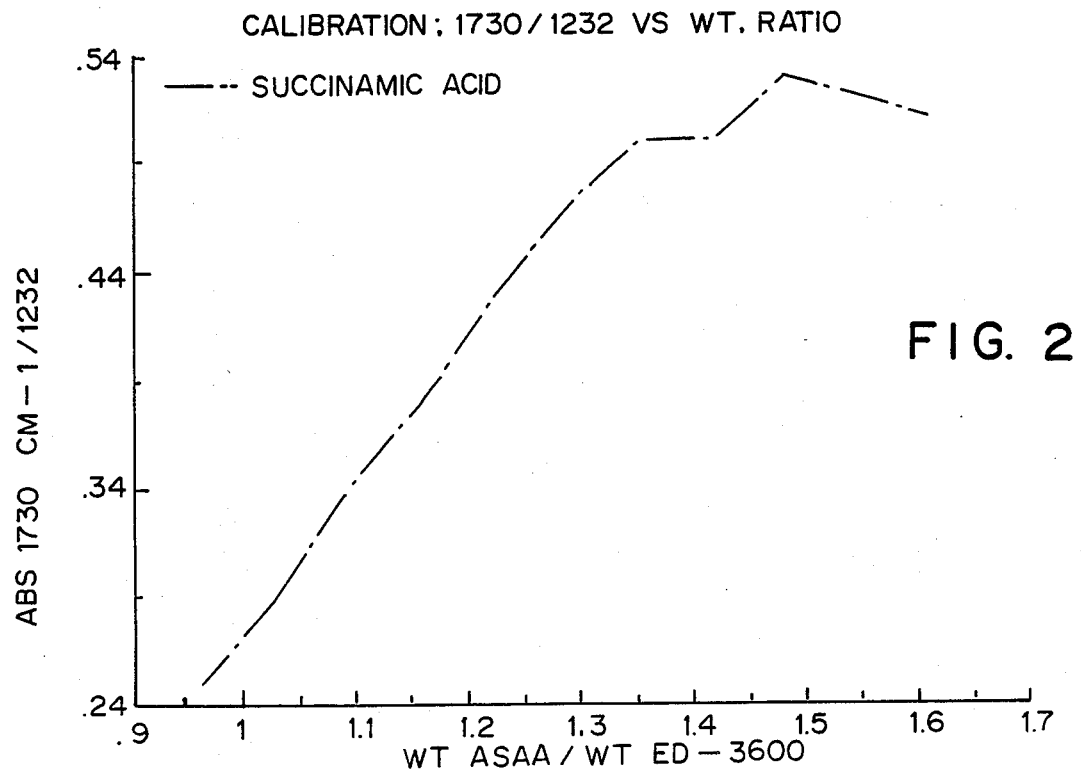
FIG.2 is a graph, i.e., second curve, showing the relationship of the optimum reactant IR absorption ratio versus the optimum reactant weight ratio as to succinamic acid.
Figure 3:
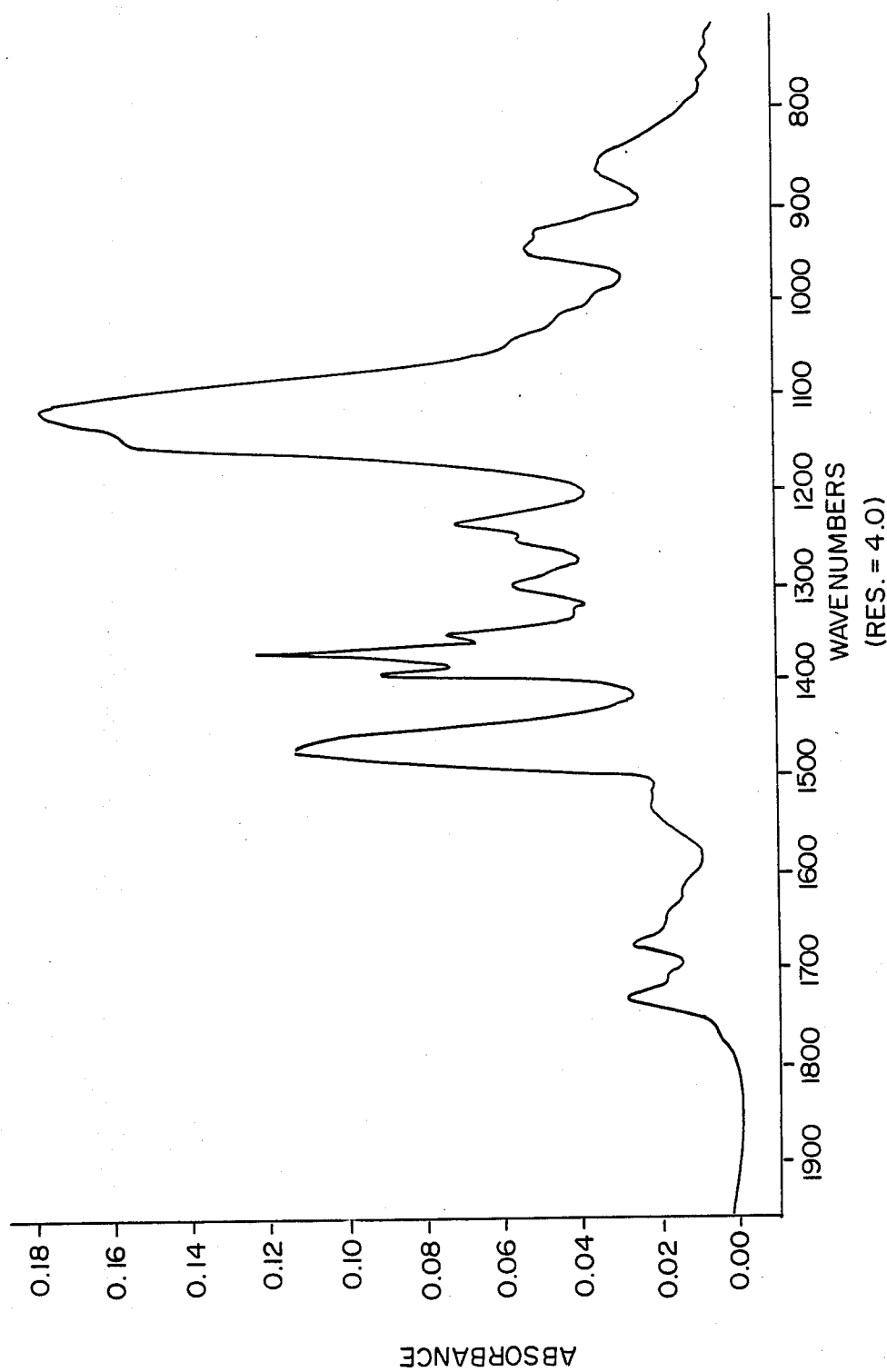
FIG.3 is a graph showing the spectrometry determination of the characteristic IR absorption of the product by showing the absorbance versus the wavelength of each reactant.

In the third step, it was presumed that the conditions of the reaction were known. A small scale reaction were carried out under these conditions and the IR spectra were recorded. An analysis of the spectra of the reagents and reaction mixture yielded the new absorbances due to product formation. The spectrum of the small scale reaction is shown in FIG.3. Then, the spectra in FIGS. 4 and 5 were compared with the spectrum in FIG.3. The two new main absorbances were at 1731 $cm^{-1}$ and 1675 $cm^{-1}$ Thus, a characteristic peak corresponding to the product was the absorbance at 1731 $cm^{-1}$ which was used in FIG.2.

An absorbance that is characteristic to the product was chosen. A series of small scale reactions was carried out in which the weight ratio of the reactants was varied over a broad spectrum as in Step 2. The spectra of these reactions were recorded. A plot of the IR ratio of the product to reactants vs weight ratio was constructed, i.e., the second curve (FIG.2). This allowed the identifying of the weight ratio which formed the maximum amount of product to be made (see FIG.1).

The IR ratio of the weight ratio of reactants which formed the maximum amount of product could be obtained from FIG.1.

In Step 4, the reactor for the large scale reaction was charged with this optimum weight ratio. The IR spectrum was measured prior to heating to insure that the proper weight ratio had been added. Corrections, if necessary, were done at this point before the reaction proceeded.

By following this procedure, it was assured that the large scale reaction would yield the maximum amount of product the first and every time.

According to the present invention, the weight ratio of the reactants ranges from about 1.3 to about 1.4, the preferred weight ratio being about 1.35. The characteristic IR absorption characteristic of the functional groups respectively is about 1250 $cm^{-1}$ for the diamine (1) and 1232 $cm^{-1}$ for the anhydride (2). The characteristic IR absorption for the desired product, i.e., the ORI control additive, an alkenyl succinimide, is at 1706 $cm^{-1}$.

The optimum IR absorption ratio of the functional groups of ethylene oxide of the diamine (1) and polyisobutenyl (PIB) of the anhydride and free PIB (2) ranges from about 2.0 to about 2.2 while the optimum IR absorption of the product, an alkenyl succinimide, at 1706 $cm^{-1}$ is maximized.

It is understood that one skilled in the art may develop inventions related to that described above. However, the scope of the present invention is defined and limited to that covered by the appended claims.

We claim:

1. A method of predetermining the exact weight ratio of the reactants polyethoxy polypropoxy polybutoxy diamine and an alkenyl succinic anhydride to provide a maximum ORI additive alkenyl succinimide, said method comprising:
    (a) determining by spectrometry the characteristic IR absorption of the functional groups of each reactant and that of the product desired;
    (b) establishing the weight ratio to the IR absorption ratio of the reactants to produce the desired product whereby a first curve is formed of the reactant IR absorption ratio versus the reactant weight ratio;
    (c) varying the weight ratio of the reactants in simulated small scale reactions of the method to produce the product and using the product characteristic IR absorption to form a second curve of the product IR absorption versus the reactant weight ratio, thereby determining the reactant weight ratio necessary to produce the maximum amount of said product;
    (d) using the reactant weight ratio determined from the second curve, determine from said first curve the optimum IR absorption ratio of the functional groups of said reactants; and
    (e) comparing the prior measured IR absorption ratio of the reactant mixture being charged with said determined optimum reactant IR absorption ratio, whereby the exact weight ratio of the reactants is measured prior to heating and, if necessary, corrected to produce the maximum amount of the product.

2. The method of claim 1 wherein the functional groups measured, respectively, of the diamine and the anhydride are ethylene oxide and polyisobutenyl and the respective IR absorption of each functional group is 1232 $cm^{-1}$ and 1250 $cm^{-1}$.

3. The method of claim 1 wherein the reactant weight ratio ranges from about 1.3 to about 1.4 and the reactant IR absorption ratio determined at the end of step c in claim 1 ranges from about 2.0 to about 2.2.

4. The method of claim 1 wherein optimum IR absorption characteristic of the product is about 1706 $cm^{-1}$.

5. The method of claim 1 wherein the exact weight ratio determined at the end of step c in claim 1 of the reactants is about 1.35.

6. The method of claim 1 where the anhydride is a $(C_{33}-C_{330})$ alkenyl succinic anhydride and said succinimide is a $(C_{33}-C_{330})$ alkenyl succinimide.

7. The method of predetermining the exact weight ratio of the reactants polyethoxy polypropoxy polybutoxy diamine and a $(C_{33}-C_{330})$ alkenyl succinic anhydride to provide a maximum amount of the ORI additive alkenyl succinimide, said method comprising:

(a) determining by spectrometry the characteristic IR absorption of the functional groups of said reactants polyethoxy polypropoxy polybutoxy diamine and $(C_{33}-C_{330})$ alkenyl succinic anhydride that of the ORI control additive alkenyl succinimide;

(b) establishing the weight ratio to the IR absorption ratio of said reactants polyethoxy polypropoxy polybutoxy diamine and $(C_{33}-C_{330})$ alkenyl succinic anhydride to produce the ORI control additive of alkenyl succinimide, whereby a first curve is formed of the reactant IR absorption ratio versus the reactant weight ratio;

(c) varying the weight ratio of the reactants in simulated small scale reactions of the method to produce the ORI control additive and using the optimum ORI control additive IR absorption versus the reactant weight ratio thereby determining the reactant weight ratio necessary to produce the maximum amount of said ORI control additive;

(d) using the reactant weight ratio determined from the second curve, determine from said first curve the optimum IR absorption ratio of the functional groups of said reactants polyethoxy polypropoxy polybutoxy diamine and $(C_{33}-C_{330})$ alkenyl succinic anhydride; and (e) comparing the prior measured IR absorption ratio of the reactant mixture being charged with said determined optimum reactant IR absorption ratio, whereby the exact weight ratio of the reactants is measured prior to heating and, if necessary, corrected to produce the maximum amount of the product.

* * * * *